United States Patent
Hei et al.

(10) Patent No.: US 7,008,913 B2
(45) Date of Patent: Mar. 7, 2006

(54) AROMATIC SUBSTITUTED NONIONIC SURFACTANTS IN SOIL PREVENTION, REDUCTION OR REMOVAL IN TREATMENT ZONES

(75) Inventors: Robert D. P. Hei, Baldwin, WI (US); Michael E. Besse, Golden Valley, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 10/968,265

(22) Filed: Oct. 18, 2004

(65) Prior Publication Data

US 2005/0054875 A1  Mar. 10, 2005

Related U.S. Application Data

(63) Continuation of application No. 09/995,367, filed on Nov. 27, 2001.

(51) Int. Cl.
- *C11D 7/54* (2006.01)
- *C01B 15/10* (2006.01)
- *C02F 1/72* (2006.01)
- *A61K 33/40* (2006.01)

(52) U.S. Cl. ............ 510/310; 252/186.26; 252/186.42; 210/759; 424/616

(58) Field of Classification Search ................ 424/616; 210/759; 510/310, 303; 252/186.26, 186.42; 423/226

See application file for complete search history.

(56) References Cited

U.S. PATENT DOCUMENTS

| | | |
|---|---|---|
| 4,374,104 A | 2/1983 | Primack |
| 4,421,664 A | 12/1983 | Anderson et al. |
| 4,443,342 A | 4/1984 | Stas et al. |
| 4,448,705 A | 5/1984 | Gray |
| 4,508,537 A | 4/1985 | Fenton et al. |
| 4,595,577 A | 6/1986 | Stas et al. |
| 4,743,447 A | 5/1988 | Le Rouzic et al. |
| 4,874,540 A | 10/1989 | Greenwald et al. |
| 4,997,450 A | 3/1991 | Olson et al. |
| 5,026,503 A | 6/1991 | Stewart |
| 5,039,447 A | 8/1991 | Reuben |
| 5,122,538 A | 6/1992 | Lokkesmoe et al. |
| 5,139,788 A | 8/1992 | Schmidt |
| 5,200,189 A | 4/1993 | Oakes et al. |
| 5,234,719 A | 8/1993 | Richter et al. |
| 5,268,002 A | 12/1993 | Olson et al. |
| 5,314,687 A | 5/1994 | Oakes et al. |
| 5,336,500 A | 8/1994 | Richter et al. |
| 5,370,708 A | 12/1994 | Olson et al. |
| 5,409,713 A | 4/1995 | Lokkesmoe et al. |
| 5,419,908 A | 5/1995 | Richter et al. |
| 5,436,008 A | 7/1995 | Richter et al. |
| 5,437,868 A | 8/1995 | Oakes et al. |
| 5,451,346 A | 9/1995 | Amou et al. |
| 5,484,549 A | 1/1996 | Hei et al. |
| 5,489,434 A | 2/1996 | Oakes et al. |
| 5,505,915 A | 4/1996 | Copeland et al. |

(Continued)

FOREIGN PATENT DOCUMENTS

| | | |
|---|---|---|
| EP | 0 596 493 A1 | 5/1994 |
| GB | 930584 | 7/1963 |
| GB | 1 370 678 | 10/1974 |
| GB | 2 132 630 | 11/1984 |
| JP | 52127487 | 10/1977 |

(Continued)

OTHER PUBLICATIONS

"Handbook of Industrial Chemical Additives", An International Guide by Product, Trade Name Function, and Supplier, Compiled by Michael and Irene Ash, VCH Publishers New York (1991), entries for Triton CF-10 and Triton DF-12, on p. 550.*

(Continued)

*Primary Examiner*—Joseph D. Anthony
(74) *Attorney, Agent, or Firm*—Merchant & Gould P.C.

(57) ABSTRACT

Disclosed is a process for the treatment of a plant gaseous stream containing odor compounds including hydrogen sulfide, an alkyl mercaptan or an alkyl thiol and mixtures thereof by contacting the plant stream with an oxidizing agent that reduces the odor but forms elemental sulfur. The elemental sulfur, and other inorganic, scales that form, or deposit, can be suppressed or removed using a specific aromatic substituted nonionic surfactant material. The use of such a process produces a significant improvement in odor quality while maintaining a clean process facility and low operating pressure drop.

6 Claims, No Drawings

U.S. PATENT DOCUMENTS

| | | |
|---|---|---|
| 5,545,374 A | 8/1996 | French et al. |
| 5,567,444 A | 10/1996 | Hei et al. |
| 5,578,134 A | 11/1996 | Lentsch et al. |
| 5,616,335 A | 4/1997 | Nicolle et al. |
| 5,630,985 A | 5/1997 | Williams et al. |
| 5,674,538 A | 10/1997 | Lokkesmoe et al. |
| 5,712,239 A | 1/1998 | Knowlton et al. |
| 5,733,474 A | 3/1998 | Kagermeier et al. |
| 5,756,139 A | 5/1998 | Harvey et al. |
| 5,861,096 A | 1/1999 | Mason et al. |
| 5,900,256 A | 5/1999 | Scoville et al. |
| 6,015,536 A * | 1/2000 | Lokkesmoe et al. ........ 423/210 |
| 6,168,808 B1 | 1/2001 | Hamon Godin et al. |
| 6,183,708 B1 | 2/2001 | Hei et al. |
| 6,197,784 B1 | 3/2001 | Fuchs et al. |
| 6,254,801 B1 | 7/2001 | Reinold et al. |
| 6,257,253 B1 | 7/2001 | Lentsch et al. |
| 6,277,344 B1 | 8/2001 | Hei et al. |
| 6,302,968 B1 | 10/2001 | Baum et al. |
| 6,326,032 B1 | 12/2001 | Richter et al. |
| 6,444,230 B1 | 9/2002 | Godin et al. |

FOREIGN PATENT DOCUMENTS

| | | |
|---|---|---|
| JP | 03190995 | 8/1991 |
| JP | 4-108513 | 4/1992 |

OTHER PUBLICATIONS

"Develop a Nose for Odor Control", Chemical Engineering, Oct. 1993, pp. 20-23, 27.

"Peroxygens in environmental protection", Fraser, Effluent and Water Treatment Journal, Jun. 1986, pp. 186-199.

"Removal of $No_x$ and $SO_2$ from Flue Gas by Peracid Solutions", Littlejohn et al., Ind. Eng. Chem. Res., 1990, 29, pp. 1420-1424.

"New Treatment Schemes Control Odors", Mellvaine, WATER/Engineering & Management, Jan. 1990, pp. 28-31.

"Odors: The Other Effluent", Pope et al., Civil Engineering, Aug. 1989, pp. 42-44.

International Search Report for PCT/US 98/27820, filing date Dec. 30, 1998.

U.S. Appl. No. 09/114,017, filed Jul. 10, 1998 (Lokkesmoe et al.), now abandoned.

* cited by examiner

AROMATIC SUBSTITUTED NONIONIC SURFACTANTS IN SOIL PREVENTION, REDUCTION OR REMOVAL IN TREATMENT ZONES

This application is a continuation of application Ser. No. 09/995,367, filed Nov. 27, 2001, now abandoned, which application is incorporated herein by reference.

FIELD OF THE INVENTION

The invention relates to the use of specific aromatic nonionic surfactant materials to prevent the formation of or remove soils such as an inorganic soil. The material can be used to remove soils from a variety of surfaces, (i.e.) from reaction zones, treatment zones or other soil accumulation areas. The compounds of the invention are useful in removing elemental sulfur in simple or complex soils from soiled surfaces. More particularly, the aromatic nonionic surfactant materials can be used in columns or scrubbers used in a gas treatment for the prevention of the formation of or removal of inorganic soils such as elemental sulfur or carbon soils, phosphate soils carbonate, silicate soils or other soils of complex mixture. The aromatic surfactants are used to remove sulfur, in an elemental form commonly found in combination with other soils, from surfaces within the gas treatment equipment. The invention relates to the maintenance of or the restoration of substantial pressure dropped a treatment zones for gaseous streams that can be compromised by soil formation

BACKGROUND OF THE INVENTION

The formation of or accumulation of soils on hard surfaces or in a treatment zone is undesirable for both esthetic and operational reasons. Sulfur soils can be unsightly. Further, such soils can often reduce the efficiency of the chemical treatment for the overall treatment efficiency of a treatment zone. Treatments that can prevent the formation of or remove soils from a treatment zone can substantially improve operating efficiencies. Both organic and inorganic soils can accumulate in a variety of chemical treatment zones. Inorganic soils can be particularly troublesome. Such soils can include nonionized soils such as elemental sulfur, elemental carbon, etc. Such soils can also include anionic or cationic soils. Important soils include soils comprising carbonates ($CO_3^{-2}$), silicates ($Na_2O \cdot xSiO_2$), sulfates ($SO4^{-2}$), sulfites ($SO3^{-2}$), sulfides ($S_x^{-2}$, x=1–8), elemental sulfur, phosphates, ($HPO_4^{-2}$, $PO_4^{-3}$, etc.), or mixtures thereof.

In one embodiment of the use of such treatment zones, the treatment of a gas streams for the purpose of removing hydrogen sulfide and other mercaptan compounds is common. In natural gas processing, ethylene, propylene, flue gas, industrial gas is effluents and other commercial gas streams commonly containing hydrogen sulfide and mercaptan odor ingredients can be treated for contaminate removal. Further, industrial plants, agricultural installations, hospitals, kitchens, etc. that handle large quantities of organic material such as hog farms, dairy farms, chicken farms, meat packing plants, animal rendering plants, composting plants, paper mills, sewage treatment plants and other similar installations can generate large quantities of odors that typically exit the facility in an odor contaminated atmospheric effluent flume or other effluents. Such an effluent can contain a large variety of odoriferous or odor causing inorganic and organic chemicals or molecules including organic sulfides or organic thiols (mercaptans), monoamines, diamines, triamines, ammonia, alcohols, formaldehyde, acetaldehyde, carboxylic acids, skatole, carbon disulfide and hydrogen sulfide and other odor forming oxidizable compounds. An atmospheric effluent having one or more of such compounds can have a strong odor and can be highly objectionable within the plant to plant personnel and outside the plant to plant neighbors. In many gas treatment facilities, hydrogen sulfide and related mercaptan materials are contented with oxidizing agents that under common processing conditions result in the formation of elemental sulfur ($S°$). This sulfur can form a deposit, commonly in combination with other soils such as inorganic soils, organic soils, hardness components of service water, and other materials that can associate with the elemental sulfur in a soil deposit. Such soils can rapidly plugged in the gas transport tabs within the treatment structure. Such plugging reduces the volume of gas that can be treated, increases the pressure drop within the equipment and increases the cost of operating the gas transport device. The ability to inhabit sulfur deposit formation, or if deposits are present, to remove sulfur deposit is an important goal.

An odor is a gas phase emission that produces an olfactory stimulus. The odor thresholds of many chemicals that act as odor compositions common throughout the chemical process industries include, for example, ethyl sulfide having an odor threshold in the atmosphere of 0.25 parts per billion (ppb), hydrogen sulfide with an odor threshold of 0.4 ppb, dimethyl sulfide with an odor threshold of 1.0 ppb, ethyl mercaptan with an odor threshold of 1.0 ppb, methyl mercaptan with an odor threshold of 1.1 ppb. With a low threshold a small amount of these and similar odors common in plant effluent are serious olfactory problems. Such odors result from processing large quantities of organic materials and are generated by the action of micro-organisms in any biologically active system on a source of organic material producing the odors. There are many other sulfur odor producing chemicals possible, however, as shown in this representative, non-inclusive list:

1. Sulfur Compounds
   Hydrogen Sulfide Thiophene
   Carbonyl Sulfide Isobutyl Mercaptan
   Methyl Mercaptan Diethyl Sulfide
   Ethyl Mercaptan n-Butyl Mercaptan
   Dimethyl Sulfide Dimethyl Disulfide
   Carbon Disulfide 3-Methylthiophene
   Isopropyl Mercaptan Tetrahydrothiophene
   tert-Butyl Mercaptan 2,5-Dimethylthiophene
   n-Propyl Mercaptan 2-Ethylthiophene
   Ethyl Methyl Sulfide Diethyl Disulfide Other sources of voter are present in many gas is effluents. These odor sources are not capable forming elemental sulfur deposits however they can no big a part of the deposit and can in certain circumstances in proved a the tendency of a sulfur to form deposits.

2. Organic Nitrogen Compounds
   Primary amines
   secondary amines
   tertiary amines
   pyridines
   amides
   ammonia 3. Organic Oxygen Compounds (Oxo-Hydrocarbon Compounds)
   primary alcohols
   carboxylic acids
   aldehydes ketone compounds
phenolics Attempts have been made to reduce the production of the odor compounds and to reduce the release of the odor compounds from plants. Robinson, "Develop a Nose for Odor Control", *Chemical Engineering News*, October 1993 contains a generic disclosure of odor problems and conventional odor control using aqueous treatment compositions including $H_2O_2$, $FeCl_3$, $KMnO_4$, NaOH and others. Careful control over the organic materials within the plant and reduction of microbial populations within the plant have been attempted to reduce the generation of the odor compounds in the plant atmosphere. Attempts to scrub the odor compounds from the plant atmosphere have been made using a variety of simple absorptive and oxidizing scrubbing materials. Fragrance chemicals that simply mask the offensive odors have been tried. In fact, essential oils have been used previously as odor masking compounds.

Sodium hydroxide (NaOH), activated carbon are useful absorptives. Oxidizing materials such as ozone ($O_3$), chlorine dioxide ($ClO_2$), sodium hypochlorite (NaClO) and others have been attempted. Some degree of success has been achieved using these oxidative materials to remove organic odor molecules from atmospheric effluents. While chlorine dioxide has had some success, chlorine dioxide is highly toxic, difficult to handle and must be generated on site. Such difficulties lead to substantial resistance to its use. Further, hydrogen peroxide is also known for odor control. Hydrogen peroxide by itself is not effective against a broad range of odor constituents without additional treatment materials. However, the application of oxidative technologies including ozone, hydrogen peroxide, chlorine dioxide and other oxidants have had some limited success.

The use of peroxyacid materials in microbiological methods are also known. For example, Grosse-Bowing et al., U.S. Pat. Nos. 4,051,058 and 4,051,059 disclose peroxyacetic containing antimicrobial compositions. Stas et al., U.S. Pat. Nos. 4,443,342 and 4,595,577 disclose the treatment of waste water and waste gases containing dialkyldisulfides by metal catalytic oxidation of these compounds by means of a peroxide compound in an aqueous medium. Lokkesmoe, U.S. Pat. No. 5,409,713 teaches peroxyacetic materials as microorganism sanitizers or growth inhibitors in aqueous transport systems typically containing produce and large amounts of challenged soil load.

Fraser, in "Peroxygens in environmental protection", *Effluent and Water Treatment Journal*, June 1986 disclose that hydrogen peroxide ($H_2O_2$) can be used to reduce odor. Fraser only discusses microbial control with peroxyacetic acid and does not correlate odor control to peroxyacid treatment or concentration. Littlejohn et al., "Removal of $NO_x$ and $SO_2$ from Flue Gas by Peroxyacid Solutions", *Ind. Eng. Chem. Res.* Vol. 29, No. 7, pp. 1420–1424 (1990) disclose peroxyacids in removing nitric oxides and sulfur dioxide from coal fire derived flue gas.Lokkesmoe et al., U.S. Pat. No. 6,015,536, issued Jan. 18, 2000; Hei et al., U.S. Pat. No. 6,183,708, issued Feb. 6, 2001 and Hei et al., U.S. Pat. No. 6,277,344, issued Aug. 21, 2001 teach aspects of peracid odor reduction.

Peroxyacetic acid, neat and in aqueous solutions containing peroxyacetic acid has a strong pungent oxidizing odor resembling but stronger than acetic acid. Such materials have not been seriously considered as odor reducing materials because of the nature of its odor. The concern being that in any treatment process using a significant amount of peroxyacetic acid, the resulting treated effluent would inherently obtain the pungent odor of the peroxyacetic acid. Further, peroxyacetic acid solution inherently contain large amounts of acetic acid (HOAc).

Generally, the method of reducing odor involves using oxidizing agent to oxidizing the order component to a substantially reduced odor or odor free component. The oxidizing agent is presumed to act to oxidize many of the components of the gaseous stream. Hydrogen sulfide and many (—SH) sulfur compounds are oxidize to elemental sulfur using the following reaction sequence.

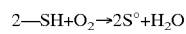

$$2\text{—SH}+O_2\rightarrow 2S°+H_2O$$

The theoretical reaction sequence (due to the empty valence in the —SH group) demonstrates that hydrogen sulfur compounds can be oxidized to elemental sulfur. This inorganic sediment, often along with other inorganic sediments including carbonates, carbon soot, phosphates, sulfates, etc., can yield substantial scale deposits in odor control systems. Consequently, there remains a need for sulfur containing gas treatment processes that avoid formation of elemental sulfur, and other inorganic materials, in the oxidizing systems.

BRIEF DISCUSSION OF THE INVENTION

The invention involves compositions and processes used in removing a soil residue from a surface. The invention can use the materials for treating a variety of operating units such as a treatment or reaction zone including a gas treatment zone. The invention further involves compositions and processes used in preventing the formation of a soil residue in a treatment zone. Such a soil residue can comprise elemental soils such and sulfur or carbon, ionic soils including anionic and cationic soils, including carbonate, silicate, phosphate in soils combining mixtures thereof. The invention involves a process for removing sulfur odor compounds from an atmospheric plant fluid effluent using oxidizing process in the presence of a specific aromatic nonionic surfactant material, used for the purpose of the preventing the formation of or removing a soil residue from a treatment zone.

The aromatic nonionic surfactant material comprises:

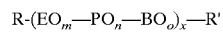

$$R\text{-}(EO_m\text{—}PO_n\text{—}BO_o)_x\text{—}R'$$

wherein EO comprises ethylene oxide, PO comprises propylene oxide and BO comprises butylenes oxide moieties or residues; m is 2 to 60, o and n are independently 0 to 40; R is a benzyl group, an alkylaryl group or, if $1 \leq o+n \leq 20$, R is a $C_{1-18}$ alkyl group; R' is a benzyl group, an alkylaryl group or, if $o+n \leq 1$, R' is a —H group; and x is 1–6. Most preferably, m is 5 to 25, o and n are independently 0 to 15; R is a benzyl group; R' is a benzyl group; and x is 1–4. The material can be used in a variety of concentrations in a concentrate used to prepare use solutions. In the cleaning process of the invention when contacte with a soiled surface, the aromatic nonionic surfactant material is commonly used in aqueous solution a concentration of about 1 to 5000 ppm, preferably about 2 to 1500 ppm, most preferably about 5 to 800 ppm of surfactant in the aqueous solution. The aqueous solution can comprise a variety of other active ingredients in combination with the aromatic nonionic surfactant.

In a process of the invention, a cleaning solution comprising the surfactant of the invention is contacted with the soil. Preferably the soil contaminate in a treatment zone is contacted with the cleaning solution for the purpose of preventing formation of or removing a soil residue from the treatment zone. In a further process of the invention, the plant atmosphere or other effluent is contacted with an aqueous treatment solution containing a controlled amount of a peroxyacid and optionally one or more fragrant essential oils. Sufficient peroxyacid is used to control odor but not contribute a peroxyacid or acid smell to the treated effluent. The process is typically conducted in a batch or continuous treatment mechanism such as a falling film contactor, a wet scrubber or venturi mechanism. A fluid effluent includes both a liquid and a gaseous effluent. The peroxyacid material comprises an effective amount of the aromatic nonionic surfactant material to prevent the formation of or remove soils that form in a treatment zone.

Surprisingly, neither the aromatic nonionic surfactant material, the peroxyacid, nor the essential oils are destroyed by the processing conditions at a rate that interferes with oxidative odor reduction or soil removal. Using a combination of a peroxyacid and an essential oil, surprisingly, allows the essential oil to behave as both a masking agent and an odor chemical reactant that augments the oxidative capacity of the peroxyacid; especially towards sulfur containing malodorous compounds. Accordingly, the invention can be found in a process for removing an inorganic or organic soil, scale, or sediment from a pre-soiled atmosphere treatment device, such as an air scrubber. The process comprising contacting the atmosphere treating system with an aqueous solution of the aromatic nonionic surfactant; and removing at least a portion of the used treatment. In the process soil residues can be prevented or routinely removed from a scrubber system.

Additionally, the invention can be found in an in situ process for simultaneously removing an odor and sediment from an atmosphere and liquid effluent, the process comprising contacting an atmosphere effluent comprising an odor component with an aqueous peroxyacid treatment composition, the aromatic nonionic surfactant to the invention and optionally one or more essential oils, forming an oxidized odor component and dissolving or dispersing the oxidized odor component or an odor component in the aqueous treatment composition to form a used treatment; and removing at least a portion of the used treatment. In the process of removing the odor component from the effluent, soil residues can concurrently be prevented or removed.

Further, the invention may also be found in a process for removing an odor from a liquid effluent, the process comprising contacting the liquid effluent comprising an odor component with an aqueous peroxyacid treatment composition combined with the aromatic nonionic surfactant composition and optionally one or more essential oils, forming a combined effluent and aqueous treatment composition having reduced odor; and removing at least a portion of the combined composition.

In the treatment of gaseous effluent, when a gaseous atmospheric effluent gas phase contacts the finely divided aqueous treatment phase, oxidizable odor molecules and particulates from the gas phase react with the oxidizing peroxyacetic acid material combined with the aromatic nonionic surfactant material and the optional essential oil in the aqueous treatment, are either chemically converted into freely soluble compounds, or dispersed aqueous-based particulates, and are scrubbed from the gas phase. Specifically, the gas molecules and particulate matter contact a liquid droplet, the odor causing compounds and particulates transfer from the gas phase into the liquid phase and are then reacted with the peroxyacetic acid and/or essential oil to form water soluble, low volatile compounds or dispersed particles. Other soluble components of the gas phase simply are solubilized in the acidic aqueous phase. The resulting atmospheric effluent has a substantially reduced concentration of odor compound or composition and has a less objectionable odor level. As a result of the use of the aromatic nonionic surfactant material, the treatment zone's are left substantially void of accumulated soils. For the purpose of this application, the term "active oxygen", "active species" and "active ingredients" are substantially synonymous and refer to the total concentration of peroxide, peroxyacid or other available oxidizing species in a treatment that can oxidize the odor molecules or components. For the purpose of this disclosure the symbols EO, PO and BO, respectively, refer to ethylene oxide, propylene oxide and butylene oxide. The term "ppm" means that the reference material is present at a quantity of parts by weight per each one million parts by weight of the total composition.

The term "atmosphere effluent" relates to any gaseous stream emanating from an industrial plant, agricultural facility, hospital, institutional kitchen, doctors office, household kitchen, etc. processing organic materials that result in the release of odor molecules into the atmosphere effluent. The atmosphere effluent can contain a large variety of odoriferous or odor causing chemicals or molecules including oxohydrocarbons, organo sulfides or organic thiols (mercaptans), monoamines, diamines, triamines, ammonia, alcohols, phenolics, formaldehyde, acetaldehyde, skatole, carbon disulfide and hydrogen sulfide and other odor forming oxidizable organic compounds. Such an atmosphere effluent typically is released in a flume that moves with the atmosphere and slowly mixes into the atmosphere, becomes diluted and dispersed into the environment.

Further, not only does the peroxyacid (such as peroxyacetic acid) material result in the oxidation of odor components into freely soluble or dispersable materials that remain in the aqueous phase, we have found that the use of such an acidic material results in the absorption of organic bases such as ammonia and amines resulting in the effective scrubbing of these compounds from the atmospheric effluent material. Additionally, it is now shown that the combinations of peroxyacids, aromatic nonionic surfactant, and essential oils allows for simultaneous masking and enhanced malodor removal. In large part the process is designed to favor the mass transfer of odor compounds into the aqueous treatment.

DETAILED DISCUSSION OF THE INVENTION

The compositions and process of the invention are used to prevent the formation of or to remove soil from a treatment zone. Such treatment zones can be used for treating fluid media including a gaseous or aqueous media. In the operation of such treatment zones soils can accumulate simply by accumulating soils that contact surfaces in the treatment zone. The soils can also accumulated by oxidation or reduction reactions that can convert a gaseous material to a contaminating soil solid residue. The presence of or accumulation of such soils in a treatment zone can reduce operating efficiency or substantially increase pressure drop. The prevention of or rule of such soils can maintain or restore the unit operating efficiency.

One important treatment zone comprises a zone used to treat and atmospheric effluent. Such effluent can be treated for a variety of purposes including a removal of odors from the stream. The process of the invention uses absorption, more specifically a gas/liquid absorption or entrapment, a liquid/liquid absorption or entrapment, or solid particulate/liquid absorption or entrapment, during and after an oxidative reaction to separate odor components from a fluid effluent. Both odor and particulate materials can be absorbed or entrapped by the oxidizing liquid stream. Any odor or particular material that accumulates in the treating materials can cause the formation on or enlarge the size the soil residues in the treatment zone. In the process, absorption is driven by the solubility or dispersion of the odor compounds, and oxidized odor materials, in the aqueous phase. At the same time, a chemical reaction between an aqueous stream and a gas stream results in washing or scrubbing oxidized odor compounds or compositions from the effluent with the liquid composition. As a result of the chemical reaction between the odor molecules in the stream and the treatment liquid, one or more of the oxidized constituents of the gas mixture will preferentially dissolve or disperse in the liquid and can thus be efficiently removed. In treatment of gaseous odor, the gas constituent reacts with the oxidant to form a water soluble or dispersable material which forms a physical solution in the liquid and is removed from the gas stream.

Such a gas absorption is preferably carried out in a device where intimate contact between a gas phase and a finely divided liquid phase or a finely divided gas phase and a liquid phase is obtained. Such devices, including sparged and agitated vessels, venturi systems, filter beds, and the various types of spray towers, can contact a gas phase with a liquid and can disperse the gas phase into bubbles or foams. Spray towers are typically the most important of these since countercurrent multistage contact and other contacting can be obtained. The gas can be contacted in the form of a finely divided or small bubble into a bulk liquid in a sparged vessel (bubble column). Finely divided gas or atmospheric bubbles can be dispersed into a mechanically agitated vessel in which the liquid contents are agitated to ensure close contact with the finely divided bubbles and the liquid. Multistage absorption can be obtained using multistage tray towers using a variety of towers, baffles, barriers, downspouts and other mechanical means to ensure close contact between the gas phase and the liquid phase. Venturi scrubbers can be used along with wetted-wall towers, spray towers and spray chambers, packed towers, and any other countercurrent or cocurrent apparatus that can ensure close contact between the atmospheric or odor containing gas phase and the liquid treatment. The process can be run either continuous or in semibatch or batch mode. During the process, the accumulated treatment composition containing a substantial quantity of the odor compounds and the oxidized odor compounds are removed from the process equipment and directed to typically on-site treatment or municipal sewage treatment plants. In smaller applications, or liquid/liquid applications a venturi system is preferred while in larger applications, a countercurrent scrubber towers can be preferred.

In a countercurrent column, the oxidative and/or masking treatment solution is fed in the top of the absorber and the effluent or gas mixture enters from the bottom. The odor components of the gas reacts with and dissolves in the liquid treatment composition. The aqueous treatment composition containing the oxidized odor generating substances is removed from the bottom of the column. Conversely, in a cocurrent column both streams enter the column at one end and depart at the opposite end. In either case, the resulting treatment solution containing the scrubbed materials is then treated in an industrial, agricultural or municipal waste water treatment facility.

The vertical absorber may be a packed column operating either countercurrently or cocurrently, plate column operating either countercurrently or cocurrently, a falling film contactor or a simple spray absorption column operating cocurrently. Preferred packed columns can be shell filled with packing material designed to disperse the liquid and bring the liquid in finely divided form in close contact with the rising effluent stream. Packed columns offer simple and cheap construction and are preferred for complex or corrosive gases because packed columns can be made from ceramics or other non reactive packings. In plate towers, liquid flows from plate to plate in a cascade fashion while the effluent gas bubbles through the flowing liquid within each plate through a multitude of dispersing means or through the cascade of liquid as in a shower deck tray. These absorbers are used where tall columns are required.

The fundamental physical principles underlying the absorption of the odor molecules from the plant atmosphere effluent in a gas absorption reaction mode relates to the solubility of the reaction product between the peroxyacid (preferably peroxyacetic acid) oxidant liquid phase and the gas molecules. The rate of mass transfer is high (odor removal is efficient) because the reaction product, between the odor molecules and the organic peroxyacid oxidant, comprises molecules such as sulfate, alcohol, aldehyde, carboxylic acid and salts, ammonium ion ($NH_4^+$), protonated amines and other similar species which are highly soluble in water solutions particularly at acid pH. Since these oxidized and other non-oxidized materials are highly soluble in the aqueous treatment solutions, mass transfer principles tend to favor the dissolution of such materials in the aqueous treatment composition and result in highly efficient odor molecule scrubbing. The treatment compositions of the invention are adapted for use in commonly available scrubber systems. Such systems can be obtained from a variety of manufacturers including EST Corp., D.R. Technology, Inc., PEPCO and VIATEC. In smaller applications, a venturi contactor may be preferred.

The aqueous treatment compositions of the invention can be introduced into the wet scrubber in the form of a simple aqueous stream, an agitated stream, or a spray having an effective concentration of a peroxyacid treatment composition. The treatment compositions of the invention comprise a peroxyacid, preferably peroxyacetic acid having the formula:

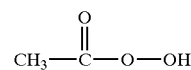

The peroxyacid is an unstable composition that is typically made by the direct acid catalyzed equilibrium oxidation reaction between 5 to 98 wt % hydrogen peroxide in contact with the liquid carboxylic acid, typically acetic acid or by auto-oxidation of aldehydes, acid chlorides, carboxylic anhydrides with hydrogen peroxide or other peroxy oxidizing compositions.

In treating liquid effluents, a batch or continuous treatment can be used. In batchwise treatment the effluent can be treated in large stirred tanks. In continuous treatment, the effluent can be treated by a continuous stream of peroxyacid that can be added in a pumped or metered treatment. One common metering scheme is to add the treatment using a venturi. In a venturi the passage of the effluent past a venturi causes the treatment to be drawn into the effluent. The ratio of addition can be controlled by a selected venturi or metering means.

Preferably, the process of the invention includes the use of a combination of peroxyacid, hydrogen peroxide and carboxylic acid. The compositions of the invention contain water, peroxyacetic acid, hydrogen peroxide and acetic acid across a relatively broad range of concentrations. Peroxyacetic acid is a freely water soluble liquid having a pungent, acrid odor resembling acetic acid, but with a strong oxidizing character. The antimicrobial compositions of the invention also comprise a proportion of hydrogen peroxide. Hydrogen peroxide in combination with the peroxyacid, preferably peroxyacetic acid, provides a surprising level of successful odor scrubbing capacity when compared to conventional scrubbers. Hydrogen peroxide apparently provides an effervescent action in the treatment composition that tends to help in providing finely divided aqueous treatment particles that improve oxidation by the peroxyacid and absorption through small particles with large surface area. The concentration of hydrogen peroxide is adjusted with respect to the concentration of carboxylic acid and water to ensure that the treatment composition contains preferably greater than about 1 ppm, preferably about 1 to 1000 ppm of residual or active peroxyacetic acid in the treatment composition for highly efficient odor molecule scrubbing. The concentration of the active ingredients in the treatment composition can be adjusted using make-up amounts of the concentrate material delivered to the continuously flowing aqueous stream during processing.

We have found that a specific class of aromatic nonionic surfactant materials can be combined, in the formula or as a $2^{nd}$ stream adjuvant, with the aqueous peroxyacid materials. Most preferably the aromatic nonionic surfactant is added as a $2^{nd}$ concentrate directly to the treatment stream. These surfactant materials are sufficiently stable such that the surfactant can maintain an effective soil removing concentration of the surfactant in any treatment liquid.

The aromatic nonionic surfactant material comprises:

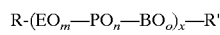

$$R\text{-}(EO_m\text{—}PO_n\text{—}BO_o)_x\text{—}R'$$

wherein EO comprises ethylene oxide, PO comprises propylene oxide and BO comprises butylenes oxide moieties or residues; m is 2 to 60, o and n are independently 0 to 40; R is a benzyl group, an alkylaryl group or, if $1 \leq o+n \leq 20$, R is a $C_{1-18}$ alkyl group; R' is a benzyl group, an alkylaryl group or, if $o+n \leq 1$, R' is a —H group; and x is 1–6. Most preferably, m is 5 to 25, o and n are independently 0 to 15; R is a benzyl group; R' is a benzyl group; and x is 1–4. The material can be used in a variety of concentrations in a concentrate used to prepare use solutions. In the cleaning process of the invention when contacte with a soiled surface, the aromatic nonionic surfactant material is commonly used in aqueous solution a concentration of about 1 to 5000 ppm, preferably about 2 to 1500 ppm, most preferably about 5 to 800 ppm of surfactant in the aqueous solution.

The oxidative composition of the invention may also comprise any number of functional and non-functional adjuvants. Specifically, the compositions of the invention may comprise stabilizing agents, wetting agents, as well as pigments or dyes among other constituents. Stabilizing agents may be added to the composition of the invention to stabilize the peroxyacid and hydrogen peroxide to prevent the premature decomposition of the oxidizing material within the composition of the invention. Chelating agents or sequestrants are generally useful in the compositions of the invention in the form of alkyl diamine polyacetic acid-type chelating agents such as EDTA, acrylic and polyacrylic acid-type agents, phosphonic acid, and phosphonate-type chelating agents among others. Preferred sequestrants include phosphonic acid and phosphonic acid salts including 1-hydroxyethylidene-1,1-diphosphonic acid, amino[tri(methylenephosphonic acid)] and other phosphonate based sequestering agents. Also useful in the compositions of the invention are wetting or defoaming agents. Wetting agents function to increase the surface area and reduce particle size of the particulate aqueous treatment composition. Such wetting agents are known within the art to raise the surface activity of the composition of the invention. Preferred wetting agents are low foaming nonionic polymeric materials that can be-used comprising ethylene oxide moieties, propylene oxide moieties as well as a mixture thereof and EO—PO heteric or block compositions. Defoaming agents comprising silica, silicones, aliphatic acids or esters, alcohols, sulfates, sulfonates, amines, amides, nonionic materials and others can be helpful in defoaming the mixture during processing. The treatment compositions of the invention may contain a number of other constituents selected by the operator to enhance the properties of the materials.

The compositions of the invention also contain one or more essential oils, which are generally defined as distillable odoriferous products of plant origin. While the principle components are mono- to tetra-unsaturated olefin terpenes, essential oils may also contain benzenoid and aliphatic compounds as well. Terpenes are unsaturated hydrocarbons which are based on the isoprene unit of alternating double bonds. Terpenes of use in the invention include citral, camphor, α and β-pinene, terpineol, limonene, α and β-terpinene, α and β-phellandrene, cedrene, geraniol, linalool, neral and abietic acid. Especially preferred terpenes include citral, camphor, α and β-pinene, terpineol and limonene. Preferred essential oils can also include such aldehydes as benzaldehyde and cinnamaldehyde.

The treatment compositions of the invention can comprise concentrate materials that comprise either one or two-part concentrates that fall within the following generic formulas:

| Ingredient | two-part concentrates | | |
|---|---|---|---|
| | Useful Wt % | Working Wt % | Preferred W % |
| Treatment Concentrate 1 | | | |
| Peroxyacid | 1–40 | 2–30 | 4–20 |
| Hydrogen Peroxide | 1–50 | 3–40 | 5–30 |
| Carboxylic Acid | 1–90 | 3–60 | 5–40 |
| Sequestrant | 0–10 | 0.1–5 | 0.5–2 |
| Water | Balance | Balance | Balance |
| Treatment Concentrate 2 | | | |
| Essential Oil | 0–100 | 0–90 | 0–85 |
| Mineral Spirits | 0–80 | 0–20 | 0–15 |
| Wetting agent or defoamer | 0–20 | 0–10 | 0–5 |
| Aromatic nonionic surfactant | 0.1–100 | 0.05–50 | 0.1–30 |

The above compositions comprise concentrate materials that can be metered into an aqueous stream directed to the scrubber apparatus. An oxidative concentrate such as treatment concentrate 1 can be metered into an aqueous stream along with separately added essential oils and aromatic nonionic surfactants (such as treatment concentrate 2) in an amount forming a residual concentration containing about 1 to 1000 ppm peroxyacid, 1 to 2,000 ppm hydrogen peroxide, 1 to 600 ppm of carboxylic acid (e.g. acetic acid) and other active components, about 1 to 4,000 ppm of aromatic nonionic surfactant, about 1 to 10,000 ppm of essential oil, preferably about 30 to 150 ppm peroxyacid, 1 to 500 ppm hydrogen peroxide, 1 to 300 ppm of carboxylic acid and other active components and 10 to 500 ppm of essential oil. As a general guideline, the following table sets forth working ranges of active ingredients in the treatment composition after dilution in the aqueous stream within the wet scrubber.

Residual or Active Concentrations in the Treatment

| Treatment Constituent | Useful (ppm) | Working (ppm) | Preferred (ppm) |
|---|---|---|---|
| Peroxyacid | 1–1,000 | 5–300 | 30–150 |
| Aromatic nonionic surfactant | 1–4000 | 2–1500 | 5–800 |
| Hydrogen Peroxide | 1–2,000 | 1–1,000 | 1–500 |
| Carboxylic Acid | 1–600 | 1–400 | 1–300 |
| Sequestrant | 0.01–50 | 0.01–25 | 0.01–10 |
| Essential Oil | 1–10,000 | 5–1,000 | 10–500 |
| Water | Balance | Balance | Balance |

Another way to view composition ranges is to use ratios between various critical components. The first important ratio is that between the peroxyacid and the carboxylic acid. The aqueous peroxyacid fog treatment composition comprises less than 4 parts by weight, preferably less than 2.5 parts by weight, of carboxylic acid per each part of peroxyacid.

The second important ratio is that between hydrogen peroxide and the peroxyacid. The aqueous peroxyacid fog treatment composition comprises less than 5 parts by weight of hydrogen peroxide per each part of peroxyacid, preferably less than 2 parts by weight of hydrogen peroxide per each part of peroxyacid.

Because active oxygen can come from more than one source, it is also important to consider the total active oxygen content. The aqueous peroxyacid fog treatment composition comprises a dosed peroxyacid and hydrogen peroxide concentration resulting in an active oxygen concentration of less than about 400 parts by weight of active oxygen per one million parts of the treatment, preferably less than about 270 parts by weight of active oxygen per one million parts of the treatment and more preferably less than about 150 parts by weight of active oxygen per one million parts of the treatment.

A particularly aqueous peroxyacid fog treatment composition comprises 1 to 90 weight percent (wt %) of acetic acid, 1 to 50 wt % of hydrogen peroxide, a sequestrant, and 1 to 40 wt % of peroxyacetic acid.

These concentrations are determined using the following formulas:

$$\text{Dosed Concentration} = \frac{\text{grams of active ingredient added}}{\text{grams of liquid solution}}$$

$$\text{Residual Concentration} = \frac{\text{grams of active ingredient detected by analysis after reaction}}{\text{grams of liquid solution}}$$

During operations, in removing odor compositions from an effluent stream, a continuous stream of the treatment composition is directed to the top of a scrubber column. The treatment composition flows counter-currently through the column to scrub odor compositions from the effluent gas. It is possible, however, to accomplish this using co-current flow if using a packed column or spray chamber. To maintain an effective concentration of the peroxyacid, preferably peroxyacetic acid in the treatment composition, a make up amount of the concentrate must be either continually or intermittently added to the continuous stream to maintain at least about 1 ppm of residual peroxyacid, preferably at least about 20 and more preferably at least 35 ppm of residual peroxyacid during operations.

One-Part Concentrates

Another type of treatment composition of the invention can comprise concentrate materials that comprise one-part concentrates that fall within the following generic formulas:

Exemplary peroxyacetic acid formulas (equilibrium mixtures) include those in tables 1 to 4:

TABLE 1

| Ingredient | Wt % |
|---|---|
| Acetic Acid | 32.0 |
| Aromatic nonionic surfactant | 5.0 |
| Hydrogen Peroxide | 11.1 |
| Sequestrant | 1.5 |
| Peroxyacetic Acid | 15.0 |
| Water | balance |

TABLE 2

| Ingredient | Wt % |
|---|---|
| Acetic Acid | 6.5 |
| Aromatic nonionic surfactant | 10.0 |
| Hydrogen Peroxide | 26.6 |
| Sequestrant | 1.0 |
| Peroxyacetic Acid | 4.7 |
| Water | balance |

TABLE 3

| Ingredient | Wt % |
|---|---|
| Acetic Acid | 30.0 |
| Aromatic nonionic surfactant | 30.0 |
| Hydrogen Peroxide | 7.0 |
| Sequestrant | 1.0 |
| Peroxyacetic Acid | 5.0 |
| Peroctanoic Acid | 0.5 |
| Hydrotrope (coupling agent) | 5.0 |
| Octanoic Acid | 3.0 |
| Water | balance |

TABLE 4

| Ingredient | Wt % |
|---|---|
| Acetic Acid | 46.0 |
| Aromatic nonionic surfactant | 5.0 |
| Hydrogen Peroxide | 4.0 |
| Sequestrant | 1.0 |
| POAA (Peroxyacetic acid) | 12.0 |
| POOA (Peroxyoctanoic acid) | 2.0 |
| Octanoic Acid | 8.2 |
| Water | balance |

During operations to maintain the concentrations of the peroxyacid mentioned above, the exemplary peroxyacid formulations are typically dosed as make-up to the treatment streams at rates of about 100 to 2000 ppm of the peroxyacetic acid, and about 1 to 4,000 ppm of aromatic nonionic surfactant, formulations in the aqueous stream typically flowing as make-up water at the rate of about 1 to 10,000 L-min$^{-1}$. The use of make-up solution directed to the continuously flowing treatment stream is a preferred means to introduce the peroxyacetic acid material into the scrubber or venturi apparatus.

Process Parameters

In the odor reduction treatment process of the invention, an aqueous solution is passed in a continuous stream through the scrubber apparatus. In typical applications, the aqueous treatment composition passes through the scrubber at a rate of about 1 to 10,000 L-min$^{-1}$, depending upon the size of the scrubber. Typically, the scrubber is a vertical wet scrubber having interior packing. The aqueous solution passes through the column packing in a finely divided form comprising streams, droplets, etc. through the column packing. The rate of solution flow is adjusted depending upon the size of the scrubber, the volumetric flow rate of gas, and the soil level of the gas.

The aqueous treatment material is added to the continuously flowing aqueous stream in make-up water. The aqueous peroxyacid material, preferably peroxyacetic acid, is typically added in a concentrate at a dosed concentration of about 1 to 1000 ppm, preferably about 30 to 150 ppm of peroxyacetic acid to make-up water added to the aqueous stream at a rate of about 1 to 500 liters per hour. The effective residual concentration of peroxyacid, preferably peroxyacetic acid, in the aqueous stream is maintained between 1 and 1,000 ppm peroxyacetic acid, preferably about 1 to 150 ppm peroxyacetic acid, most preferably about 30 to 80 ppm peroxyacetic acid. The effective residual concentration of aromatic nonionic surfactant, preferably a benzyl capped alcohol ethoxylate/propoxylate or a dibenzyl ethoxylate/propoxylate, in the aqueous stream is maintained between 1 and 4,000 ppm aromatic nonionic surfactant, preferably about 2 to 1500 ppm aromatic nonionic surfactant, most preferably about 5 to 800 ppm aromatic nonionic surfactant. The effective concentration of essential oils is maintained at a concentration of 0 to 10,000 ppm, preferably 10 to 500 ppm. The atmospheric effluent from the plant atmosphere is passed through the scrubber at a rate of about 100 to 3 million liters of atmosphere effluent per minute (atmos. L-min$^{-1}$). The temperature of the scrubber is maintained at ambient temperatures, however, somewhat elevated temperatures can enhance the oxidation and dissolution of the gas in the liquid stream. The wet scrubber can be operated continually at such ratios to efficiently remove odor compounds from the atmospheric stream. The odor compounds and oxidized odor compounds remain solubilized in the aqueous phase. After the odor reduction process is used for some period, the odor compounds are removed with a portion of the aqueous stream that can be removed from the scrubber continually. Such a proportion of the aqueous stream can comprise about 1 to 500 liters of the aqueous stream per hour (L-hr$^{-1}$). Alternatively, the aqueous stream can be removed batchwise or in its entirety periodically, e.g. every 4, 6, 12 or 24 hours, bi-weekly, weekly, etc. The process can then be restarted with fresh water and fresh treatment chemicals. The aqueous product of the treatment process is a relatively dilute solution of the treatment chemicals, sulfates, ammonia, alcohols, aldehydes and other common waste water components. The aqueous effluent resulting from the process is compatible with most industrial and municipal waste treatment facilities which can treat the aqueous effluent rendering it innocuous to the environment.

In general, one cubic foot of plant atmosphere effluent is contacted with about 0.01 to 10 liters of aqueous treatment solution. Preferably, at least about 20% of an odor forming compound selected from the group consisting of an oxohydrocarbon, organomercaptan, an amine, ammonia, hydrogen sulfide or mixtures thereof, is absorbed and removed in the process from the plant atmosphere effluent and wherein the odor threshold is reduced by at least 20%.

WORKING EXAMPLE 1

Scale Control on Plastic Parts

The objective of this example was to evaluate a variety of nonionic structural features for effecting inorganic scale removal from plastic parts. It was desired to establish a correlation between scale control, scale removal, HLB, and foaminess.

The unexpected results are shown in Table 1. First, the best (<90%) inorganic-sulfur scale removal was found for benzylated noninoics (experiments 1–3). However, benzylation is not an exclusive feature for performance since the alkylated benzyl-ethoxylate of experiment 9 proved to be ineffective for scale removal. This is evidenced by comparing the benzylated experiments vs. their uncapped homologues; cf., experiments 1 vs. [10 or 7 or 13], 2 vs. 11 and 3 vs. 5. Note that the benzylated nonionic of experiment 9 performed much worse than the non-benzylated homologue of experiment 6.

Also, the presence of propoxylation—in combination with aromatic moieties in the molecule (alkyl-aryl, benzylation)—appears to aid in scale removal; cf., experiments [2 or 4] vs. [7, 8, 10–13].

No correlation to the hydrophile/lipophile balance (HLB) or foam control (cloud points) can be demonstrated. Both are often used in the art as performance markers for detergency. For example, experiment 1 with a low HLB, excellent scale removal and foam reduction is in contrast to experiments 10, 12 or 14 which have low HLB's but yield poor scale removal but moderate-to-excellent foam control. Also, experiment 2 with a high HLB and excellent scale removal and foam height control in contrast to experiments 7 or 13 which also have high HLB's but poor scale performance but excellent foam control.

TABLE 1

Inorganic Scale Control on Plastic Parts Using Nonionic Surfactants

| 1 | 2<br>Surfactant<br>(500 ppm active surfactant) | 3<br>Hydrophilic/<br>lipophile<br>balance<br>(HLB) | 4<br>Inorganic<br>Sulfur<br>Removal<br>(%)[1] | 5<br>Foam<br>Height<br>Reduction<br>(%)[2] |
|---|---|---|---|---|
| 1 | benzyl-(PO)$_z$—(EO)$_x$—(PO)$_y$—(EO)$_x$—(PO)$_z$-benzyl | 2–4 | 99% | 100% |

TABLE 1-continued

Inorganic Scale Control on Plastic Parts Using Nonionic Surfactants

| 1 | 2<br>Surfactant<br>(500 ppm active surfactant) | 3<br>Hydrophilic/<br>lipophile<br>balance<br>(HLB) | 4<br>Inorganic<br>Sulfur<br>Removal<br>(%)[1] | 5<br>Foam<br>Height<br>Reduction<br>(%)[2] |
|---|---|---|---|---|
| 2 | n-alkyl-$(PO)_y$—$(EO)_x$-benzyl | 10–11 | 97% | 84% |
| 3 | alkylaryl-O—$(EO)_x$-benzyl | 13–15 | 92% | 52% |
| 4 | alkylaryl-O—$(EO)_x$—$(PO)_y$H | 9–11 | 91% | 59% |
| 5 | alkylaryl-O—$(EO)_x$—H | 8–9 | 77% | 39% |
| 6 | n-alkyl-$(EO)_x$—H | 8–9 | 58% | 50% |
| 7 | H—$(PO)_y$—$(EO)_x$—$(PO)_y$—H | 12–18 | 24% | 100% |
| 8 | n-alkyl-$[(PO)_y/(EO)_x]$—$(PO)_z$ | 6–8 | 24% | 41% |
| 9 | n-alkyl-$(EO)_x$-benzyl | 4–6 | 19% | 64% |
| 10 | H—$(PO)_z$—$(EO)_x$—$(PO)_y$—$(EO)_x$—$(PO)_z$—H | 3–5 | 11% | 86% |
| 11 | n-alkyl-$(PO)_y$—$(EO)_x$—H | 5–7 | 8% | 84% |
| 12 | $[H—(PO)_y—(EO)_x—H]_2$—NCH2CH2N—$[—(EO)_y—(PO)_x—H]_2$ | 1–7 | 8% | 100% |
| 13 | H—$(EO)_x$—$(PO)_y$—$(EO)_x$—H | 12–18 | 7% | 91% |
| 14 | branched-alkyl-$(EO)_x$—H | 7–9 | 1% | 86% |

[1]Weight % removal vs. an unsoiled scrubber packing membrane after 1 hour without agitation.
[2]Foam height % reduction vs. a control study using nonylphenolethoxylate (9.5 EO).

WORKING EXAMPLE 2

Scale Control in Air Scrubbing Equipment

The objective of this example was to compare the industrial plant air scrubbing process which uses no surfactants—for scale control—to one which uses an aromatic capped nonionic surfactant. The evaluation was done in an industrial feather hydrolyzer air scrubber which operates with a continuously increasing scale loading, in the piping and packing materials, that must be cleaned on a monthly basis. When the test began the piping was about 50% plugged and the packing material about 20% with a scale that was, analyzed and, found to be >96% elemental sulfur with some inorganic carbonates. The differential pressure of the malodorous air stream was 4.6 psi.

For the control study, a standard air scrubbing program using chlorine gas and sodium hydroxide was run; maintaining a pH>11.0 and a titratable chlorine level of >500 ppm. The system was pre-inspected in the scrubber piping and packing material. The system was run for time periods of 15 minutes and 1 hour; after which the equipment was inspected. Similarly, for the nonionic surfactant cleaning program, 500 ppm of a di-benzylated modified ethylene oxide/propylene oxide surfactant was supplied—without other adjuvants—into the aqueous scrubber and run for the same time periods. The results are shown in Table 2, and indicate the substantial improvement in scale removal of the current art over traditional treatment programs. Complete removal of the inorganic scale was induced within 1 hour of operation using the nonionic; vs. no removal using the standard treatment method. The yield of inorganic sulfur scale removed by the novel process was about 600 pounds, vs. less than 0.5 pound for the other procedure. Additionally, the air flow differential pressure was improved by more than 25% using the current art; while no change was found for the traditional process.

TABLE 2

Inorganic Scale Control Usng A Benzylated Nonionic Surfactant

| 1 | 2<br>Surfactant | 3<br>Scale<br>Removal<br>Time<br>(minutes)[1] | 4<br>Scrubber<br>Differential<br>Pressure<br>(psi) | 5<br>Inorganic Sulfur<br>Removal (%) | |
|---|---|---|---|---|---|
| 1 | control[2] | 0 | 4.6 | 0% | 0% |
|   |  | 15 | — | 0% | 0% |
|   |  | 60 | 4.6 | 0% | 0% |
| 2 | benzyl-$(PO)_z$—$(EO)_x$—$(PO)_y$—$(EO)_x$—$(PO_z)$-benzyl[3] | 0 | 4.6 | 0% | 0% |
|   |  | 15 | — | 60% | >80% |
|   |  | 60 | 3.4 | 100% | 100% |

[1]Operational time of the air scrubbing system with water recirculation on and malodorous air passing through at 75,000 cfm.
[2]Control experiment using a conventional chlorine/sodium hydroxide air scrubbing program without added nonionic surfactants.
[3]500 ppm active surfactant

WORKING EXAMPLE 3

Carbonate and Silicate Control in Air Scrubbing Equipment

The objective of this example was to test additional inorganic soils deposited on air scrubbing equipment. The evaluation was done in an industrial room air scrubber which continuously removes malodorous gases and particles from carcass cooking and blood drying operations. When the test began the scrubber surface and packing material were completely covered with a whitish scale to a depth of about 0.9 cm. This scale had been analyzed by IR and EDS and was found to be about 30% calcium cabonate and about 70% inorganic metal silicates. The system was pre-inspected in the scrubber piping and packing material. The nonionic, 500 ppm of a di-benzylated modified ethylene oxide/propylene oxide, surfactant was supplied without other adjuvants into the aqueous scrubber and the system was run for about 9 hours with intermittent inspections. The results are shown in Table 3, and indicate essentially complete removal of the inorganic scale was induced within 9 hours of operation using the nonionic; vs. no removal using a standard treatment method of chlorine and caustic soda.

TABLE 3

Carbonate and Silicate Scale Removal Using a Benzylated Noninoinc Surfactant

| 1 | 2<br>Surfactant | 3<br>Scale<br>Removal Time<br>(minutes)[1] | 4<br>Carbonate,<br>Silicate Scale<br>Removal (%) |
|---|---|---|---|
| 1 | control[2] | 0 | 0% |
|   |  | 105 minutes | 0% |
|   |  | 555 minutes | 0% |
| 2 | benzyl-(PO)$_z$—(EO)$_x$—(PO)$_y$—<br>(EO)$_x$—(PO)$_z$-benzyl[3] | 0 | 0% |
|   |  | 105 minutes | 33% |
|   |  | 555 minutes | >95% |

[1]Operational time of the air scrubbing system with water recirculation on and malodorous air passing through at 75,000 cfm.
[2]Control experiment using a conventional chlorine/sodium hydroxide air scrubbing program without added nonionic surfactants.
[3]500 ppm active surfactant These data demonstrate that the aromatic nonionic surfactant materials disclosed in this invention have the capacity for removing a variety of soils from hard surfaces. While the experimental data were accumulated by monitoring soil removal and gas treatment facilities, we believe that these data demonstrate the soil removing capacity of these aromatic surfactant materials. In this data, the aromatic nonionic surfactant materials have been shown to the capable of removing elemental sulfur, carbon, silicate, carbonate, and phosphate soils from hard surfaces located within the treatment units. Further this data clearly demonstrates that surfactants without the specific aromatic nonionic structure plane in the application have substantially poorer soil removing capacity. Since the cleaning capacity of the experimental materials in this data set is not apparently affected by the use of peracid materials, we believe the soil removing capacity shown in this data is directed to and derived from the presence of the aromatic nonionic surfactant in an aqueous solution.

The specification, data and examples provide an explanation of the operating parameters of the invention and provide a basis to understand the use of aromatic nonionic surfactant materials in soil removal from hard surfaces. Further, using aromatic nonionic surfactant materials in removing soil in processes for odor reduction is also explained. The technology of the application can have a variety of applications other than the specifics set forth in this application. Accordingly the invention is found in the claims hereinafter appended.

We claim:

1. An aqueous peracid treatment composition, adapted for the removal of an odor composition from a gaseous stream, the treatment composition comprising, in an aqueous medium,
    an effective odor reducing amount of a peracid composition comprising hydrogen peroxide, peracetic acid and a carboxylic acid;
    about 0.1 to 25 weight percent of a sequestrant composition;
    an effective amount of an odor reducing essential oil; and
    about 1 to 40 weight percent of an effective soil removing amount of a surfactant composition selected from the group consisting of:
        benzyl-(PO)$_z$-(EO)$_x$-(PO)$_y$-(EO)$_x$-(PO)$_z$-benzyl;
        alkylaryl-O-(EO)$_x$-benzyl;
        and mixtures thereof;
    wherein x is 2–60; y is 0–15; and z is 0–15 and $1 \leq y+z \leq 40$.

2. The composition of claim 1 wherein the soil is elemental sulfur.

3. The composition of claim 2 wherein the aqueous treatment composition comprises about 0.1 to 50 weight percent of a peracetic acid composition.

4. The composition of claim 1 wherein the composition is adapted for removal of an odor comprising a sulfur compound from a gaseous stream.

5. The composition of claim 1 wherein the aqueous treatment composition comprises about 1.0 to 20 weight percent of a peracetic acid composition and about 0.1 to 20 weight percent of the surfactant.

6. The composition of claim 5 wherein the aqueous treatment composition comprises about 0.1 to 10 weight percent of a sequestrant composition.

* * * * *